(12) United States Patent
Ohnishi

(10) Patent No.: US 9,006,285 B2
(45) Date of Patent: Apr. 14, 2015

(54) THERAPEUTIC AGENT FOR HEPATITIS C

(75) Inventor: Haruo Ohnishi, Chiba (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 175 days.

(21) Appl. No.: 13/121,645

(22) PCT Filed: Sep. 30, 2009

(86) PCT No.: PCT/JP2009/067066
§ 371 (c)(1),
(2), (4) Date: Mar. 29, 2011

(87) PCT Pub. No.: WO2010/038796
PCT Pub. Date: Apr. 8, 2010

(65) Prior Publication Data
US 2011/0184064 A1    Jul. 28, 2011

(30) Foreign Application Priority Data
Sep. 30, 2008  (JP) ................................. 2008-254084

(51) Int. Cl.
| | | |
|---|---|---|
| A61K 31/22 | (2006.01) | |
| A61K 31/20 | (2006.01) | |
| A61K 38/00 | (2006.01) | |
| A61K 31/202 | (2006.01) | |
| A61K 31/232 | (2006.01) | |
| A61K 38/21 | (2006.01) | |

(52) U.S. Cl.
CPC ............. *A61K 31/202* (2013.01); *A61K 31/232* (2013.01); *A61K 38/21* (2013.01)

(58) Field of Classification Search
CPC ... A61K 31/202; A61K 31/232; A61K 38/21; A61K 2300/00
USPC .................................................. 514/560, 4.3
See application file for complete search history.

(56) References Cited

U.S. PATENT DOCUMENTS

| | | |
|---|---|---|
| 2003/0153513 A1 | 8/2003 | Shiomi et al. |
| 2006/0069070 A1 | 3/2006 | Fiorucci et al. |
| 2006/0088502 A1* | 4/2006 | Sata et al. .................... 424/85.4 |

FOREIGN PATENT DOCUMENTS

| | | |
|---|---|---|
| JP | 2007-529427 A | 10/2007 |
| WO | WO 02/09757 A1 | 2/2002 |
| WO | WO 2004/073706 A1 | 9/2004 |
| WO | WO 2008/041665 A1 | 4/2008 |

OTHER PUBLICATIONS

Takaki et al. "Eicosapentaenoic acid could permit maintenance of the original ribavirin does in chronic hepatitis C virus patients during the first 12 weeks of combination therapy with pegalated interferon-alpha and ribavirin," Intervirology, 2007, vol. 50, pp. 439-446.*
International Search Report, PCT/JP2009/067066, Nov. 2, 2009.
Kapadia et al., "Hepatitis C virus RNA replication is regulated by host geranylgeranylation and fatty acids", Proceedings of the National Academy of Sciences of the United States of America, Feb. 15, 2005, vol. 102, No. 7, pp. 2561-2562, 2564-2566.
Leu et al., "Anti-HCV activities of selective polyunsaturated fatty acids", Biochemical and Biophysical Research Communications, vol. 318, No. 1, pp. 275-280, 2004.
Malaguarnera et al., "Fish Oil Treatment of Interferon-Alpha-Induced Dyslipidaemia: Study in Patients with Chronic Hepatitis C", BioDrugs, vol. 11, No. 4, pp. 285-291, Apr. 1999.
Moriya et al., "Increase in the Concentration of Carbon 18 Monounsaturated Fatty Acids in the Liver with Hepatitis C: Analysis in Transgenic Mice and Humans", Biochemical and Biophysical Research Communications, vol. 281 No. 5, pp. 1207-1212, 2001.
Poynard et al., "Effect of Treatment With Peginterferon or Interferon Alfa-2b and Ribavirin on Steatosis in Patients Infected With Hepatitis C", Hepatology, vol. 38, No. 1, pp. 75-85, Jul. 2003.
Yano et al., "Comprehensive Analysis of the Effects of Ordinary Nutrients on Hepatitis C Virus RNA Replication in Cell Culture", Antimicrobial Agents and Chemotherapy, vol. 51, No. 6, pp. 2016-2027, Jun. 2007.
Kapadia et al., "Hepatitis C virus RNA replication is regulated by host geranylgeranylation and fatty acids", Proceedings of the National Academy of Sciences of the United States of America, Feb. 15, 2005, vol. 102, No. 7, pp. 2561-2566.
English translation of International Preliminary Report on Patentability in PCT/JP2009/067066 mailed on May 19, 2011.
Anonymous, "Hepatitis C's Interferon Resistance Mechaniern Discovered," HHMI—Research News (Jul. 1, 1999), pp. 1-2.
Caslera et al. "Hepatitis C Virus-induced Hepatocellular Steatosis," Am. J. Gastroenterol (2005), vol. 100, pp. 711-715.
Extended European Search Report issued Jul. 27, 2012, in European Patent Application No. 09817828.8.
Sekiya et al. "Polyunsaturated Fatty Acids Ameliorate Hepatic Steatosis in Obese Mice by SREBP-1 Suppression," Hepatology (2003), vol. 38, pp. 1529-1539.
Shen et al., "Application of Nutrigenomics in HCV Hepatosteatosis: Impact of Food Factors-Gene Interactions," The Open Nutraceuticals Journal (2009), vol. 2, pp. 107-112.
Tomioka et al., "Effects of Eicosapentaenoic Acid Supplements in the Treatment of Chronic Hepatitis C Patients," J. Nutr. Sci. Vitaminol. (2005), vol. 51, pp. 419-425.

* cited by examiner

*Primary Examiner* — Shengjun Wang
(74) *Attorney, Agent, or Firm* — Birch, Stewart, Kolasch & Birch, LLP

(57) ABSTRACT

Disclosed is a novel therapeutic means against interferon-resistant hepatitis C. Specifically disclosed are: a pharmaceutical composition for treating interferon-resistant hepatitis C, which is characterized by comprising at least one component selected from the group consisting of an ω-3 polyunsaturated fatty acid, a pharmaceutically acceptable salt of the fatty acid and an ester of the fatty acid as an active ingredient; and a method for utilizing the pharmaceutical composition.

17 Claims, No Drawings

THERAPEUTIC AGENT FOR HEPATITIS C

TECHNICAL FIELD

The present invention relates to pharmaceutical compositions for treating hepatitis C, and methods of treating hepatitis C.

BACKGROUND ART

In 30 to 40% of acute hepatitis cases attendant on hepatitis C virus (HCV) infection, HCV will not be detectable in time, leading to the normalization of hepatic function, while in 60 to 70% thereof, patients with acute hepatitis become HCV carriers, that is to say, develop hepatitis C. The probability that hepatitis C goes into spontaneous remission is extremely low, 0.2%, and 10 to 16% of hepatitis C cases progress to cirrhosis 20 years on average after the primary infection. In cirrhosis cases, hepatocellular carcinoma occurs at a high annual rate of not less than 5%. It is inferred that, if patients with hepatitis C aged 40 years are left without any appropriate treatment until the age of 70, 20 to 25% of them develop hepatocellular carcinoma. The annual mortality of liver cancer is over 30,000 in total, and is still increasing, whereupon about 80% of the dead had hepatitis C (Non-Patent Document 1).

Under these circumstances, it is a national task to treat and cure hepatitis C, and the administration of interferon (IFN)-α alone or in combination with ribavirin is generally performed as a treatment for hepatitis C. It, however, is said that the HCV elimination rate is about 30% for IFN-α alone, and about 40% if IFN-α and ribavirin are administered in combination. A poorer effect of interferon therapy on hepatitis C is argued from two points of view. Specifically, there is a problem with the genotype of HCV. Hepatitis C may clear up after treatment merely in one per three patients with genotype 1 hepatitis C, and two per three patients with genotypes 2 and 3 hepatitides C (Non-Patent Literature 2).

Another problem dwells in hepatic steatosis. Hepatic steatosis in hepatitis C is different from that in simple fatty liver or hepatitis B in that C18:1 fatty acids, such as oleic acid (18:1(9)) and vaccenic acid (18:1(11)), are accumulated in larger amounts. HCV is considered to cause fatty liver specific to hepatitis C by affecting a particular pathway in the lipid metabolism (Non-Patent Literature 3).

In hepatitis C, the presence of hepatic steatosis weakens the therapeutic effect of an antiviral agent on hepatitis C. By a combined application of IFN-α and ribavirin, sustained virological response (SVR) was achieved in 66% of the patients not having hepatic steatosis, but in 50% on average of the patients having hepatic steatosis (Non-Patent Literature 4).

In hepatitis C in which hepatic steatosis is very likely to be observed, the therapeutic effect of an antiviral agent on hepatitis C is thus weakened if hepatic steatosis is present, which suggests that not only HCV elimination but some measures against hepatic steatosis are required in the treatment of hepatitis C.

Hepatic steatosis in hepatitis C and HCV core protein are involved in each other. The HCV core gene transgenic mice had such a hepatic lipid composition that C18:1 fatty acids were accumulated in larger amounts than in the mice having simple obesity. Similar difference in hepatic lipid composition was observed between fatty liver patients with HCV infection and those without HCV infection (Non-Patent Literature 3).

On the other hand, HCV core protein attaches to lipid droplets accumulated in the liver by the HCV core protein, and forms new HCV around the lipid droplets (Non-Patent Literature 5).

In other words, in hepatitis C, HCV core protein conducts lipid accumulation or steatosis in the liver through a unique process differing from the process of any other type of fatty liver, and lipids accumulated in the liver promote HCV proliferation. HCV proliferation and hepatic steatosis are exacerbation factors in each other, that is to say, there exists a cycle of hepatitis C exacerbation between HCV proliferation and hepatic steatosis. Nothing but the breakage of the cycle of hepatitis C exacerbation is necessary for the optimization of the treatment of hepatitis C.

Polyunsaturated fatty acids (PUFAs) are defined as those fatty acids each of which has a plurality of carbon-carbon double bonds in the molecule, and classified as ω-3 fatty acids, ω-6 fatty acids, and so forth in accordance with the positions of double bonds. Exemplary ω-3 polyunsaturated fatty acids (ω-3 PUFAs) include α-linolenic acid, icosapentaenoic acid (EPA), and docosahexaenoic acid (DHA).

It is reported that polyunsaturated fatty acids such as arachidonic acid, EPA and DHA inhibited HCV replication in a cell culture system using Ava5 cells (Non-Patent Literature 6).

It is also reported on the case of using OR6 cells that, out of linoleic acid, arachidonic acid, EPA and DHA, only linoleic acid had the HCV replication-inhibiting effect which is independent of cytotoxicity (Non-Patent Literature 7), so that it has been controversial whether EPA and DHA have the HCV replication-inhibiting effect on not.

There is a report on the administration of ω-3 PUFAs additional to interferon therapy in the treatment of hepatitis C. When the interferon administered group and the group to which interferon plus ω-3 PUFAs were administered were compared with each other, the serum HCV-RNA level was reduced in both groups significantly as compared with that before administration, and the degree of reduction did not differ significantly between the groups (Non-Patent Literature 8). In terms of hypertriglyceridemia occurring as a side effect of interferon therapy, it is reported in the same article that ω-3 PUFAs had an effect of ameliorating hypertriglyceridemia due to interferon therapy.

In addition, it is reported that EPA can prevent anaemia during combination therapy with interferon and ribavirin (Patent Literature 1).

The reports as above indicate that ω-3 PUFAs are effective at relieving various side effects of interferon therapy for hepatitis C. At the same time, they imply that administration of ω-3 PUFAs did not have direct effects on the treatment of hepatitis C in itself.

CITATION LIST

Patent Literature

Patent Literature 1: WO 2004/073706

Non-Patent Literature

Non-Patent Literature 1: Tetsuro SUZUKI, Infectious Diseases Weekly Report Japan, 6(12): 11-14, National Institute of Infectious Diseases, 2004 (issued in the twelfth week of the year 2004).

Non-Patent Literature 2: Lee, C. A., Haemophilia, 6(s1): 133-137, 2000.

Non-Patent Literature 3: Moriya, K. et al., Biochemical and Biophysical Research Communications, 281(5): 1207-1212, 2001.

Non-Patent Literature 4: Poynard, T. et al., Hepatology, 38(1): 75-85, 2003.

Non-Patent Literature 5: Miyanari, Y. et al., Nature Cell Biology, 9(9): 1089-1097, 2007.

Non-Patent Literature 6: Leu, G. Z. et al., Biochemical and Biophysical Research Communications, 318(1): 275-280, 2004.

Non-Patent Literature 7: Yano, M. et al., Antimicrobial Agents and Chemotherapy, 51(6): 2016-2027, 2007.

Non-Patent Literature 8: Malaguarnera, M. et al., BioDrugs, 11(4): 285-291, 1999.

SUMMARY OF INVENTION

Technical Problems

It is conventional as a treatment for hepatitis C to administer IFN-α alone or in combination with ribavirin. With such a conventional treatment, however, viral extermination is still impossible in about a half of the patients, and the relief from side effects is far from satisfactory. It has therefore been sought to take new measures for the improvement in response rate to interferon therapy, provide a novel therapeutic agent with less side effects, and to provide patients unresponsive to interferon therapy with a novel therapeutic means.

Solution to Problems

The inventor of the present invention found that, if an ω-3 polyunsaturated fatty acid, EPA ethyl ester in particular, is continuously administered to the hepatitis C patient who was non-responder to interferon therapy, or the hepatitis C patient in whom relapse occurred after interferon was transiently effective, a therapeutic effect on hepatitis C is achieved. The inventor also found that a continuous administration of an ω-3 polyunsaturated fatty acid, EPA ethyl ester in particular, improves the response rate to interferon therapy, so as to complete the present invention. Among others, the inventor found for the first time that the unresponsiveness to interferon therapy is increased in a group of patients having hepatitis C complicated with hypertriglyceridemia, and found that the ω-3 polyunsaturated fatty acid, EPA ethyl ester in particular, as administered to such patients improves the response rate to interferon therapy.

The present invention provides the pharmaceutical composition as described below.

(1) A pharmaceutical composition for treating interferon-resistant hepatitis C, containing as an active ingredient at least one selected from the group consisting of ω-3 polyunsaturated fatty acids, pharmaceutically acceptable salts and esters thereof.

(2) The pharmaceutical composition according to (1) as above, wherein the interferon-resistant hepatitis C is complicated with hepatic steatosis.

(3) The pharmaceutical composition according to (1) as above, wherein the interferon-resistant hepatitis C is complicated with hypertriglyceridemia.

(4) The pharmaceutical composition according to any one of (1) through (3) as above, which is applied to the patient who did not respond to interferon therapy.

(5) The pharmaceutical composition according to any one of (1) through (4) as above, which is applied to the patient in whom relapse occurred after interferon therapy was transiently effective.

(6) A pharmaceutical composition for improving the response rate to interferon therapy in patients with hepatitis C, containing as an active ingredient at least one selected from the group consisting of ω-3 polyunsaturated fatty acids, pharmaceutically acceptable salts and esters thereof.

(7) The pharmaceutical composition according to (6) as above, wherein the hepatitis C is complicated with hepatic steatosis.

(8) The pharmaceutical composition according to (6) as above, wherein the hepatitis C is complicated with hypertriglyceridemia.

(9) The pharmaceutical composition according to any one of (6) through (8) as above, which is applied to the patient who did not respond to the interferon therapy.

(10) The pharmaceutical composition according to any one of (6) through (8) as above, which is applied to the patient in whom relapse occurred after the interferon therapy was transiently effective.

(11) The pharmaceutical composition according to any one of (6) through (10) as above, wherein the at least one selected from the group consisting of ω-3 polyunsaturated fatty acids, pharmaceutically acceptable salts and esters thereof begins to be administered at least two weeks before the interferon therapy.

(12) The pharmaceutical composition according to any one of (1) through (11) as above, containing as the active ingredient at least one compound selected from the group consisting of icosapentaenoic acid, docosahexaenoic acid, α-linolenic acid, pharmaceutically acceptable salts and esters thereof.

(13) The pharmaceutical composition according to any one of (1) through (12) as above, containing as the active ingredient ethyl icosapentate.

The present invention also provides the following methods.

(14) A method of treating interferon-resistant hepatitis C, which includes administering a pharmaceutical composition containing as an active ingredient at least one selected from the group consisting of ω-3 polyunsaturated fatty acids, pharmaceutically acceptable salts and esters thereof.

(15) The method according to (14) as above, wherein the interferon-resistant hepatitis C is complicated with hepatic steatosis.

(16) The method according to (14) as above, wherein the interferon-resistant hepatitis C is complicated with hypertriglyceridemia.

(17) The method according to any one of (14) through (16) as above, which is applied to the patient who did not respond to interferon therapy.

(18) The method according to any one of (14) through (17) as above, which is applied to the patient in whom relapse occurred after interferon therapy was transiently effective.

(19) A method of improving the response rate to interferon therapy in patients with hepatitis C, which includes administering a pharmaceutical composition containing as an active ingredient at least one selected from the group consisting of ω-3 polyunsaturated fatty acids, pharmaceutically acceptable salts and esters thereof.

(20) The method according to (19) as above, wherein the hepatitis C is complicated with hepatic steatosis.

(21) The method according to (19) as above, wherein the hepatitis C is complicated with hypertriglyceridemia.

(22) The method according to any one of (19) through (21) as above, which is applied to the patient who did not respond to the interferon therapy.

(23) The method according to any one of (19) through (22) as above, which is applied to the patient in whom relapse occurred after the interferon therapy was transiently effective.

(24) The method according to any one of (19) through (23) as above, wherein at least one selected from the group consisting of ω-3 polyunsaturated fatty acids, pharmaceutically acceptable salts and esters thereof begins to be administered at least two weeks before the interferon therapy.

(25) The method according to any one of (14) through (24) as above, which includes administering a pharmaceutical composition containing as the active ingredient at least one compound selected from the group consisting of icosapentaenoic acid, docosahexaenoic acid, α-linolenic acid, pharmaceutically acceptable salts and esters thereof.

(26) The method according to any one of (14) through (25) as above, which includes administering a pharmaceutical composition containing as the active ingredient ethyl icosapentate.

In addition, the present invention provides the use of at least one selected from the group consisting of ω-3 polyunsaturated fatty acids, pharmaceutically acceptable salts and esters thereof for the manufacture of a medicament for the treatment of interferon-resistant hepatitis C. The present invention also provides the use of at least one selected from the group consisting of ω-3 polyunsaturated fatty acids, pharmaceutically acceptable salts and esters thereof for the manufacture of a medicament for the improvement in response rate to interferon therapy in patients with hepatitis C.

The present invention provides a therapeutic agent for interferon-resistant hepatitis C, containing as an active ingredient at least one selected from the group consisting of ω-3 polyunsaturated fatty acids, pharmaceutically acceptable salts and esters thereof. The present invention also provides an agent for the improvement in response rate to interferon therapy in patients with hepatitis C, containing as an active ingredient at least one selected from the group consisting of ω-3 polyunsaturated fatty acids, pharmaceutically acceptable salts and esters thereof.

The present invention provides the following uses.

(27) Use of at least one compound selected from the group consisting of ω-3 polyunsaturated fatty acids, pharmaceutically acceptable salts and esters thereof for the manufacture of a medicament for the treatment of interferon-resistant hepatitis C.

(28) The use according to (27) as above, wherein the interferon-resistant hepatitis C is complicated with hepatic steatosis.

(29) The use according to (27) as above, wherein the interferon-resistant hepatitis C is complicated with hypertriglyceridemia.

(30) The use according to any one of (27) through (29) as above, wherein the medicament is applied to the patient who did not respond to interferon therapy.

(31) The use according to any one of (27) through (30) as above, wherein the medicament is applied to the patient in whom relapse occurred after interferon therapy was transiently effective.

(32) Use of at least one compound selected from the group consisting of ω-3 polyunsaturated fatty acids, pharmaceutically acceptable salts and esters thereof for the manufacture of a medicament for the improvement in response rate to interferon therapy in patients with hepatitis C.

(33) The use according to (32) as above, wherein the patients with hepatitis C are patients having hepatitis C complicated with hepatic steatosis.

(34) The use according to (32) as above, wherein the patients with hepatitis C are patients having hepatitis C complicated with hypertriglyceridemia.

(35) The use according to any one of (32) through (34) as above, wherein the medicament is applied to the patient who did not respond to the interferon therapy.

(36) The use according to any one of (32) through (35) as above, wherein the medicament is applied to the patient in whom relapse occurred after the interferon therapy was transiently effective.

(37) The use according to any one of (32) through (36) as above, wherein the medicament begins to be administered at least two weeks before the interferon therapy.

(38) The use according to any one of (27) through (37) as above, wherein the at least one compound selected from the group consisting of ω-3 polyunsaturated fatty acids, pharmaceutically acceptable salts and esters thereof is ethyl icosapentate.

Advantageous Effects of Invention

The pharmaceutical composition of the present invention has a therapeutic effect even on hepatitis C resistant to the interferon therapy as the first choice in the treatment of hepatitis C and, accordingly, provides the patient, who did not response to interferon therapy or in whom relapse occurred after interferon treatment, with a novel therapeutic means. The pharmaceutical composition of the present invention is particularly effective for the patients having hepatitis C complicated with hepatic steatosis or hypertriglyceridemia who are highly liable to be unresponsive to interferon therapy. In addition, the pharmaceutical composition of the present invention allows the improvement in response rate to interferon therapy. This effect is prominent if the composition is administered to those hepatitis C patients being unresponsive to interferon therapy, such as patients having hepatitis C complicated with hypertriglyceridemia. The pharmaceutical composition of the present invention is a therapeutic agent for hepatitis C with a high safety and less side effects.

DESCRIPTION OF EMBODIMENTS

The present invention is detailed in the following.

1. ω-3 Polyunsaturated Fatty Acids, Pharmaceutically Acceptable Salts and Esters Thereof.

Polyunsaturated fatty acids (PUFAs) are defined as those fatty acids each of which has a plurality of carbon-carbon double bonds in the molecule, and classified as ω-3 fatty acids, ω-6 fatty acids, and so forth in accordance with the positions of double bonds. For instance, ω-3 fatty acids are the fatty acids in each of which the first double bond is located on the third carbon as counted from the methyl end side of the relevant fatty acid, while ω-6 fatty acids are the fatty acids in each of which the first double bond is located on the sixth carbon as counted from the methyl end side of the relevant fatty acid. Exemplary ω-3 PUFAs include α-linolenic acid, EPA, and DHA. Unless otherwise specified, the term "PUFAs" as used herein implies not only polyunsaturated fatty acids but pharmaceutically acceptable salts as well as derivatives such as esters, amides, phospholipids and glycerides of polyunsaturated fatty acids.

The ω-3 PUFAs to be used in the present invention may be synthetic, semisynthetic or natural products, or may be in the form of natural oil containing them. The term "natural product" as used herein means a product obtained from a natural oil containing ω-3 PUFAs by a conventional extraction or crude purification, or a product obtained by highly purifying such a product. The term "semisynthetic product" implies a polyunsaturated fatty acid produced by a microorganism or the like, and also implies the polyunsaturated fatty acid as such or the polyunsaturated fatty acid as a natural product which has been subjected to a chemical treatment such as esterification or transesterification. In the present invention, a single ω-3 PUFA or a combination of two or more ω-3 PUFAs may be used.

The ω-3 PUFAs to be used in the present invention are specifically exemplified by EPA, DHA, α-linolenic acid, pharmaceutically acceptable salts and esters thereof. Examples of pharmaceutically acceptable salts and esters include salts with inorganic bases such as sodium salt and potassium salt, salts with organic bases such as benzylamine salt and diethylamine salt, salts with basic amino acids such as arginine salt and lysine salt, as well as alkyl esters such as ethyl ester and esters of mono-, di- and triglycerides. Preferred is ethyl ester, especially EPA ethyl ester (EPA-E) and/or DHA ethyl ester (DHA-E).

The ω-3 PUFAs are not particularly limited in purity, while it is generally preferable that the ω-3 PUFAs comprise not less than 25% by weight, more preferably not less than 50% by weight, and even more preferably not less than 70% by weight, especially not less than 85% by weight, of the total fatty acids contained in the composition. In a particularly desirable embodiment, the composition of the present invention contains substantially no other fatty acids than ω-3 PUFAs. In an exemplary case where EPA-E and DHA-E are to be used, the composition ratio EPA-E/DHA-E or the ratio of the (EPA-E+DHA-E) content to the total content of the fatty acids in the composition is not particularly limited, while the composition ratio EPA-E/DHA-E is preferably 0.8 or more, more preferably 1.0 or more, and even more preferably 1.2 or more. The combination of EPA-E and DHA-E is preferably of high purity, that is to say, as an example, the ratio of the (EPA-E+DHA-E) content to the total content of the fatty acids and derivatives thereof in the composition is preferably not less than 40% by weight, more preferably not less than 55% by weight, even more preferably not less than 84% by weight, especially not less than 96.5% by weight. In this connection, it is desirable that any long-chain saturated fatty acid content is low, and any ω-6 fatty acid, particularly arachidonic acid, is low in content even though it is a long-chain unsaturated fatty acid, whereupon a content lower than 2% by weight, in particular lower than 1% by weight, is preferred.

The EPA-E and/or DHA-E as used in the pharmaceutical composition of the present invention is accompanied by less impurities unfavorable to cardiovascular events, such as saturated fatty acids and arachidonic acid, as compared with fish oils or concentrates thereof, and can exert effective actions without overnutrition or excess intake of vitamin A. In addition, the EPA-E and/or DHA-E, as being an ester, has a high oxidation stability as compared with the fish oils which are chiefly in the form of triglyceride, and allows a composition to be made adequately stable by adding a conventional antioxidant.

The EPA-E to be used may be in the form of high purity EPA-E (at least 96.5% by weight pure)-containing soft capsules available in Japan as a therapeutic agent against arteriosclerosis obliterans (ASO) and hyperlipidemia (trade name, EPADEL; manufactured by MOCHIDA PHARMACEUTICAL CO., LTD.). The mixture of EPA-E and DHA-E may be LOVAZA (manufactured by GlaxoSmithKline plc; soft capsules containing ca. 46.5% by weight EPA-E and ca. 37.5% by weight DHA-E) commercially available in the USA as a therapeutic agent against hypertriglyceridemia.

Purified fish oils may also be used as ω-3 PUFAs. Monoglycerides, diglycerides, triglycerides of ω-3 PUFAs, and combinations thereof are also included in preferable examples. A variety of commercially available products containing ω-3 PUFAs as well as salts and esters thereof, such as Incromega F2250, F2628, E2251, F2573, TG2162, TG2779, TG2928, TG3525 and E5015 (Croda International PLC, Yorkshire, England), and EPAX6000FA, EPAX5000TG, EPAX4510TG, EPAX2050TG, EPAX7010EE, K85TG, K85EE and K80EE (Pronova Biopharma, Lysaker, Norway), are also usable.

2. Treatment of Interferon-Resistant Hepatitis C.

The therapeutic effect of interferon therapy on hepatitis C is determined by conducting hepatitis C virus (HCV) testing six months after the completion of treatment so as to check whether or not the HCV-RNA level in the blood has become negative. If a hepatitis C case is negative for the HCV-RNA level in the blood six months after the termination of interferon administration, it is determined as a responder, and the disease is considered to have totally cleared up owing to the extermination of HCV (complete response). Such a situation is referred to as sustained virological response (achievement of SVR). The case which became negative for the HCV-RNA level in course of the administration of interferon, but is no more negative six months after the termination of administration is determined as a relapser (case with transient effectiveness). The case which did not become negative for the HCV-RNA level in course of the administration of interferon is determined as a non-responder. The response rate to interferon therapy can be obtained by dividing the number of responders by the total case number, and the ratio at which the HCV-RNA level became negative can be obtained by dividing the number of the cases which became negative for the HCV-RNA level by the total case number. In this regard, the negativity for the HCV-RNA level in the blood corresponds to the detection of no HCV-RNA in the blood if an HCV-RNA qualitative testing method (detection limit, 50 IU/mL) is to be employed. If a quantitative method (e.g., AMPLICOR HCV MONITOR assay, original PCR, high range PCR, RT-PCR) is to be employed for the measurement of the HCV-RNA level, the negativity can be determined by making the cutoff value appropriate to the detection sensitivity of the measuring method as employed.

The determination of the response rate to interferon therapy needs a follow-up survey for six months or longer after the completion of the therapy, that is to say, is time-consuming. The response rate can be determined earlier by using a leading index as a surrogate. For instance, the response rate to interferon therapy is expected to be increased if the reduction in viral load (reduction in blood HCV-RNA level) is significant three days after the start of the therapy. Accordingly, the reduction in viral load three days after the start of interferon therapy can be used as a leading index for the determination of the response rate to the interferon therapy. The reduction in viral load is preferably not less than 2.0 as the difference between the common logarithm value of the blood HCV-RNA level before the start of interferon therapy and the common logarithm value of the blood HCV-RNA level three days after the start of interferon therapy.

Interferon therapy is the therapy in which an interferon drug is administered alone or in combination with another drug. Examples of the interferon drug include IFN-α, IFN-β, IFN-α-2a, IFN-α-2b, consensus IFN, and PEGylated interferon (interferon with polyethylene glycol attached thereto), while another drug is exemplified by ribavirin. The dose, dosage interval and dosage period of interferon may be modified as appropriate to the condition of a patient, the symptom in question, side effects or effects of the interferon used, and so forth.

In the present invention, treatment of interferon-resistant hepatitis C is targeted at the hepatitis C case which was determined as a relapser or non-responder with respect to interferon therapy.

The pharmaceutical composition of the present invention has a therapeutic effect on interferon-resistant hepatitis C. In the present invention, the therapeutic effect refers to either one or both of 1) reduction in blood HCV-RNA level, or achievement of the negativity for the blood HCV-RNA level, and 2) resolution of hepatitis. It is preferable to have both the effects 1) and 2). If a numerical value obtained before the administration of the pharmaceutical composition of the present invention is improved by at least 10%, preferably at least 30%, and more preferably at least 50%, it is considered that the therapeutic effect is exerted. In the case of the blood HCV-RNA level, a numerical value before administration is preferably reduced by not less than 50%. Resolution of hepatitis may be evaluated using the reduction in blood alanine aminotransferase (ALT) level, the improvement in liver tissue finding, and so forth as an index.

The time at which administration of the pharmaceutical composition of the present invention is to be started is not particularly limited as long as it is after the case in question was determined as a relapser or non-responder with respect to interferon therapy. In other words, administration of the composition may be started at any time after the case in question was determined as a relapser or non-responder with respect to interferon therapy irrespective of whether or not interferon therapy is newly conducted on the case which was determined as a relapser or non-responder.

A case of interferon-resistant hepatitis C complicated with hepatic steatosis refers to one of interferon-resistant hepatitis C cases which is accompanied with hepatic steatosis. Presence of hepatic steatosis may be confirmed by diagnostic imaging (e.g., CT scanning, abdominal ultrasonography, MRI) or hepatobiopsy. In hepatobiopsy for instance, the case in question may be determined as a case of interferon-resistant hepatitis C complicated with hepatic steatosis if pimelosis is observed in not less than 30% of the area of lobules in a liver tissue image, and is of a large droplet fatty change type with lipid droplets being equal to or larger than liver cells in size. In an exemplary method for diagnostic imaging, the case in question may be determined as a case of interferon-resistant hepatitis C complicated with hepatic steatosis if a value obtained by dividing the CT value for the spleen into the CT value for the liver (liver/spleen ratio value) is not more than 0.9. The pharmaceutical composition of the present invention is particularly effective for the patients having hepatitis C complicated with hepatic steatosis who are highly liable to be unresponsive to interferon therapy. In this regard, being particularly effective refers to exerting the therapeutic effect as described above to a greater extent, and/or being therapeutically effective for hepatitis C cases at higher frequency. In terms of the lipid composition in the liver with hepatitis C that is characterized by a high proportion of C18:1 fatty acids (oleic acid and vaccenic acid) among triglyceride fractions, it is recognized that such a hepatic lipid composition is improved to reduce the proportion of C18:1 fatty acids by administering the pharmaceutical composition of the present invention.

A case of interferon-resistant hepatitis C complicated with hypertriglyceridemia refers to one of interferon-resistant hepatitis C cases which is accompanied with hypertriglyceridemia. Hypertriglyceridemia is the condition in which the blood triglyceride level is 150 mg/dL or higher. While it is known that hypertridlyceridemia may occur as a side effect of interferon therapy, the present invention is not aimed at hypertriglyceridemia due to interferon therapy. In other words, the pharmaceutical composition of the present invention is to be administered to the patient who had a blood triglyceride level of 150 mg/dL or higher before the start of interferon therapy, and was determined as a relapser or non-responder as a result of receiving interferon therapy. The inventor of the present invention found that patients having hepatitis C complicated with hypertridlyceridemia are highly liable to be unresponsive to interferon therapy, and the pharmaceutical composition of the present invention is particularly effective for such patients. It is hitherto not considered that the administration of ω-3 PUFAs has a direct influence on the treatment of hepatitis C in itself, whereas the present invention allows the treatment of hepatitis C with ω-3 PUFAs if the patients to whom the invention is to be applied are chosen as appropriate.

The primary goal of the treatment of hepatitis C is to prevent the progression to cirrhosis, and inhibit the occurrence of hepatocellular carcinoma or liver failure as a complication associated with cirrhosis. Since a sustained inflammation of the liver due to virus infection leads to cirrhosis, extermination of hepatitis C virus or resolution of hepatitis is required. A continuous resolution of hepatitis can prevent the progression to cirrhosis even if the virus is not completely exterminated. For this reason, suitably applied is the agent adapted for long-term dosage that allows the resolution of hepatitis to be continued over a long period of time. The pharmaceutical composition of the present invention, as being with high safety and less side effect, can be administered over a long period of time. Moreover, the composition makes it possible to provide the patients with hepatitis C to whom interferon therapy is hard to apply with concern over its side effects, such as elderly patients, with a novel therapeutic means. Interferon is generally administered for six months to one and a half years, with administration for a longer period of time being difficult in view of side effects. In contrast, the pharmaceutical composition of the present invention has no upper limits put on its dosage period, and can be administered lastingly as long as it is therapeutically effective.

For the purpose of relieving various side effects of interferon therapy for hepatitis C, ω-3 PUFAs may be administered in course of the administration of interferon. A combined application of interferon and ω-3 PUFAs for the relief from side effects of interferon therapy is excluded from the embodiments of the pharmaceutical composition of the present invention.

3. Improvement in Response Rate to Interferon Therapy.

In the present invention, improvement in response rate to interferon therapy is targeted at the hepatitis C cases to be subjected to interferon therapy.

The pharmaceutical composition of the present invention is capable of improving the response rate to interferon therapy in patients with hepatitis C. Improvement in response rate to interferon therapy in patients with hepatitis C refers to enhancement of the effectiveness of interferon therapy as compared with that in the patients to whom the pharmaceutical composition of the present invention was not administered. Interferon therapy, and determination of its response rate are as described in the above section 2.

The pharmaceutical composition of the present invention has an effect of changing the responsiveness of a patient with hepatitis C to interferon therapy through the incorporation of ω-3 PUFAs as active ingredients into biological tissues and cells. The efficacy of ω-3 PUFAs will fully be presented before the completion of interferon therapy conducted over several weeks to several months if the composition begins to be administered simultaneously with the start of interferon therapy. It, however, is preferable to administer the pharmaceutical composition of the present invention for at least two weeks, more preferably one month or longer, and even more preferably three months or longer, especially six months or longer, prior to interferon therapy.

The pharmaceutical composition of the present invention increases the responsiveness to interferon therapy of the patient with hepatitis C who received the composition, which allows the reduction in dosage period of interferon. It is known about interferon therapy that 1) its response rate is higher as patients became negative for the blood HCV-RNA level at an earlier time after the start of interferon administration, and 2) its response rate is enhanced by prolonging the dosage period of interferon. By the administration of the pharmaceutical composition of the present invention, 1) the blood HCV-RNA level decreases in patients, or patients become negative for the blood HCV-RNA level, at an earlier time after the start of interferon administration, and/or 2) a higher response rate is achieved even if the dosage period of interferon is shorter. Such effects allow the reduction in dosage period of interferon.

The pharmaceutical composition of the present invention may begin to be administered at the time when interferon therapy for hepatitis C is started, but preferably begins to be administered at least two weeks, more preferably at least one month, and even more preferably at least three months, especially at least six months, before the start of interferon therapy. The interferon therapy to be conducted on patients may be of any type, and may be the first therapy, or a second or further therapy, for the patients. It is particularly desirable that the patients were once subjected to interferon therapy to determine them as relapsers or non-responders, and are newly subjected to the interferon therapy. The pharmaceutical composition of the present invention may be administered successively even after the start of interferon therapy.

The target for the administration of the pharmaceutical composition of the present invention is not particularly limited as long as it is the patient with hepatitis C to be subjected to interferon therapy. Preferably, the composition is administered to those patients who were found before the start of interferon therapy to have the factor which is expected to be resistant to interferon therapy, such as hepatic steatosis or hypertriglyceridemia. The inventor of the present invention found that the response rate to interferon therapy is improved in patients having hepatitis C complicated with hyperglycemidemia by conducting the interferon therapy along with the administration of ω-3 PUFAs.

The pharmaceutical composition of the present invention can be administered to the case, which was determined as a relapser or non-responder with respect to interferon therapy, for the purpose of getting both the effects as described in the above section 2 and this section. To be more specific: The pharmaceutical composition of the present invention is administered to the case, which was determined as a relapser or non-responder with respect to interferon therapy, for the purpose of getting the effect as described in the above section 2. If the blood HCV-RNA level is reduced adequately to achieve SVR by the administration of the pharmaceutical composition of the present invention by itself, the interferon therapy no more needs to be newly conducted. If the pharmaceutical composition of the present invention does not exert the therapeutic effect on hepatitis C, or the therapeutic effect is observed but without SVR, the interferon therapy is suitably conducted again in combination with the administration of the pharmaceutical composition of the present invention. The administration of the pharmaceutical composition of the present invention changes the internal body environment of patients with hepatitis C so as to bring about a high response to subsequent interferon therapy. The composition is particularly effective for patients having hepatitis C complicated with hepatic steatosis or hypertriglyceridemia.

4. Pharmaceutical Composition and Dosage Regime.

The doses and dosage periods of ω-3 PUFAs used in the pharmaceutical composition of the present invention are made adequate to the expected actions of the drugs, and each modified as appropriate to the dosage form, dosage route, and frequency of administration per day of the relevant drug, the degree of a symptom, the body weight and age of a patient, and so forth.

In the case of oral administration, preferably 0.1 to 10 g/day, more preferably 0.3 to 6 g/day, and even more preferably 0.6 to 4 g/day, especially 0.9 to 2.7 g/day, of EPA-E and/or DHA-E, for instance, is administered at a time or in two or three portions. Whether the entire amount is administered at a time or in portions may be determined as required or desired. Administration is preferably performed during meals or after meals, with an administration just after meals (within 30 minutes after a meal) being more preferred. The period of oral administration at the above dose will be at least two weeks, preferably three months or longer, more preferably one year or longer, and even more preferably three years or longer. The dosage interval may be changed as appropriate, that is to say, administration may also be performed every other day or two or three days a week, for instance.

If EPA ethyl ester is continuously administered to a healthy male adult via the oral route, the plasma EPA level reaches a plateau in one week. In this connection, the EPA/AA (arachidonic acid) ratio is often used as a pharmacological or clinical index. In one week of administration, the plasma EPA/AA will be higher than 1.0, and about two times that before administration. In the case where such parameters are used as an index to continuous administration, the dose or the dosage interval has only to be modified so as to maintain the blood ω-3 PUFA level as measured in one week of administration, and/or make the plasma EPA/AA ratio be 1.0 or higher.

The pharmaceutical composition of the present invention has such a unique action mechanism that it is incorporated in biological tissues as a fatty acid component thereof. The ω-3 PUFAs as incorporated are considered to have an effect of changing the lipid composition of cell membrane lipid rafts to thereby suppress the activation of virus in a cell through a reaction on the host's side other than those on the immune system. Consequently, the amounts of the ω-3 PUFAs to be incorporated into biological tissues have only to be set so that the drugs may exert the expected effects, and it is also possible to set them less than the conventional doses of ω-3 PUFAs commonly used as a drug. In the case of EPA-E and/or DHA-E for instance, the daily dose is preferably not less than 0.1 g but less than 2 g, more preferably not less than 0.2 g but less than 1.5 g, and even more preferably 0.3 to 0.9 g, with a dose of 0.1 to 0.3 g being particularly preferred.

The pharmaceutical composition of the present invention may be administered as the active ingredient only, or combined with excipients suitably selected from among conventional carriers or media, vehicles, binders, lubricants, colorants, flavors, sterilized water or vegetable oils as required, as well as innoxious organic solvents or innoxious solubilizing agents (e.g., glycerin, propylene glycol), emulsifiers, suspending agents (e.g., Tween 80, gum arabic solution), isotonicities, pH-adjusting agents, stabilizers, soothing agents, corrigents, flavoring agents, preservatives, antioxidants, buffers, colorants, and the like, so as to prepare an appropriate pharmaceutical formulation. Exemplary excipients which may be contained include lactose, partially pregelatinized starch, hydroxypropylcellulose, macrogol, tocopherol, a hydrogenated oil, a sucrose ester of fatty acid, hydroxypropylmethylcellulose, titanium oxide, talc, dimethylpolysiloxane, silicon dioxide, and carnauba wax.

Since ω-3 PUFAs are of a highly unsaturated nature, it is particularly desirable to add an effective amount of an antioxidant, for instance, at least one selected from among butylated hydroxytoluene, butylated hydroxyanisole, propyl gallate, gallic acid, a pharmaceutically acceptable quinone, and α-tocopherol.

The dosage form of the formulation, as varying with the mode of combined application of active ingredients according to the present invention, is not particularly limited. The formulation may be administered to a subject orally, intravenously, intraarterially, by inhalation, rectally, intravaginally or externally, that is to say, as an oral formulation in the form of tablet, film-coated tablet, capsule, microcapsule, granule, fine granule, powder, oral liquid preparation, syrup, jelly, inhalant or the like, or as a parenteral formulation in the form of ointment, suppository, injection (emulsion, suspension, nonaqueous solution), solid injection to be emulsified or suspended before use, transfusion solution, external preparation such as endermic preparation, or the like. For those subjects who are able to take oral formulations, easy-to-take oral formulations are desirable, so that oral administration of the formulation as included in a capsule such as soft capsule and microcapsule, in tablet form, or in film-coated tablet form is particularly preferred. It is also possible to administrate the formulation orally as an enteric preparation or an extended release preparation, or as a jelly in the case of dialysis patients or patients with dysphagia.

The pharmaceutical composition of the present invention may also contain a second drug apart from ω-3 PUFAs. The second drug is not particularly limited, while preferable examples include those which do not weaken the effects of the present invention, such as a liver protection drug, a hypoglycemic agent, an antihyperlipidemic agent, an antihypertensive agent, an antioxidant, and an antiinflammatory agent.

The pharmaceutical composition of the present invention may contain a pharmaceutically acceptable vehicle in addition to active ingredients. The composition may also contain a known antioxidant, coating agent, gelling agent, corrigent, flavoring agent, preservative, antioxidant, emulsifier, pH-adjusting agent, buffer, colorant or the like as appropriate.

The pharmaceutical composition of the present invention can be prepared according to a usual manner. Powder of ω-3 PUFAs is obtained by a known method in which, for instance, an oil-in-water emulsion containing (A) EPA-E, (B) dietary fiber, (C) a starch hydrolysate and/or a reducing starch decomposition product obtained by saccharification into oligosaccharide, and (D) a water-soluble antioxidant is dried in a high vacuum, then pulverized (JP 10-99046 A). By using the powder of EPA-E thus obtained, a formulation in the form of granule, fine granule, powder, tablet, film-coated tablet, chewable tablet, extended release tablet, orally-disintegrating tablet (OD tablet) or the like can be prepared according to a usual manner. Chewable tablets may be obtained by the known method in which EPA-E is emulsified in a solution of water-soluble polymer such as hydroxypropylmethylcellulose, and the resultant emulsion is sprayed onto lactose or other excipient to form powdery glanules (JP 8-157362 A), with the granules being then compressed. Orally-disintegrating tablets may be produced in accordance with such a known method as disclosed in JP 8-333243 A, and a film preparation for oral cavity may be produced in accordance with such a known method as disclosed in JP 2005-21124 A.

The pharmaceutical composition of the present invention may be a composite formulation or set formulation including ω-3 PUFAs and ribavirin or interferon in combination.

It is desirable that the active ingredients of the pharmaceutical composition of the present invention are so released and absorbed that their pharmacological actions may be exerted. Preferably, the composite formulation of the present invention has at least one effect out of an improved active-ingredient release, enhancement of the absorbability of active ingredients, enhancement of the dispersibility of active ingredients, an improved storage stability of the formulation in itself, and enhancement of the convenience to patients taking the formulation, or improvement of the compliance of such patients.

The pharmaceutical composition of the present invention is effective at treating hepatitis C in an animal, especially mammal. Exemplary mammals include humans, livestock animals such as cows, horses and pigs, as well as domestic animals such as dogs, cats, rabbits, rats and mice, with humans being preferred subjects.

EXAMPLES

The present invention is illustrated in reference to the following examples, to which the present invention is in no way limited.

Example 1

Therapeutic Effect of EPA-E on Hepatitis C Complicated with Hepatic Steatosis

The therapeutic effect of EPA-E is confirmed employing those patients as targets who were diagnosed to have hepatitis C complicated with hepatic steatosis, and did not respond to interferon therapy for three months or longer.

To the patients from whom interferon was withdrawn for about one month after they were determined to be unresponsive to interferon therapy, 2700 mg/day of EPA-E is orally administered for three months or longer. During the testing period, it is forbidden to administer any new drug considered to effect change in hepatic function. Also forbidden is administration of interferon. If the alanine aminotransferase (ALT) activity and/or the HCV-RNA level is quantified (the latter by a COBAS AMPLICOR MONITOR assay) before EPA-E administration, as well as on the third month and the sixth month of EPA-E administration, and the values as obtained are compared with those before administration, it is confirmed that the ALT activity and/or the HCV-RNA level is reduced by not less than 10%.

Instead of the ALT activity, improvement in liver tissue finding, reduction in lipid droplet, or reduction in proportion of 18:1 fatty acids (oleic acid in particular) among liver triglyceride fractions may be confirmed.

Example 2

Improvement in Responsiveness to Interferon Therapy (2-1) Improvement in Response Rate in Re-Treatment Cases.

Employing those hepatitis C patients as targets who were determined as non-responders or relapsers after interferon therapy, it is confirmed that the response rate to the interferon therapy is improved in re-treatment cases by the administration of EPA-E.

The patients to be tested are divided into two groups, namely, EPA-E administered group and EPA-E non-administered group. To the EPA-E administered group, 1800 to 2700 mg/day of EPA-E is orally administered for three months after the patients were determined as non-responders or relapsers with respect to the interferon therapy. To the EPA-E non-administered group, none of EPA and derivatives thereof is administered during the testing period. Subsequently, the interferon therapy is conducted again on both groups. The dose, dosage interval, dosage period, and the like of interferon are specified as appropriate to the condition of a patient, side effects of the interferon, and so forth. The ratio at which the patients became negative for the HCV-RNA level is calculated six months after the completion of interferon therapy.

It is confirmed that the ratio as calculated is higher in the EPA-E administered group than the EPA-E non-administered group.

(2-2) Improvement in Response Rate in Patients Having Hepatitis C Complicated with Hepatic Steatosis.

Employing those patients as targets who are to be subjected to interferon therapy, it is confirmed that the response rate to the interferon therapy is improved by the administration of EPA-E to patients having hepatitis C complicated with hepatic steatosis.

The patients to be tested are divided into two groups, EPA-E administered group and EPA-E non-administered group. In addition, a fatty liver group and a non-fatty liver group are set up in each of the EPA-E administered group and the EPA-E non-administered group by investigating the degree of hepatic fatty change through diagnostic imaging or hepatobiopsy. To the EPA-E administered group, 1800 to 2700 mg/day of EPA-E is orally administered for at least one month before interferon therapy. To the EPA-E non-administered group, none of EPA and derivatives thereof is administered during the testing period. Subsequently, interferon therapy is conducted on each group for three months or longer. The dose, dosage interval, dosage period, and the like of interferon are specified as appropriate to the condition of a patient, side effects of the interferon, and so forth. After the termination of interferon administration, the alanine aminotransferase (ALT) activity and the HCV-RNA level are measured (the latter by a COBAS AMPLICOR MONITOR assay), and a hepatohistological test is conducted. It should be noted that EPA-E is also administered to the EPA-E group during the administration of interferon.

It is confirmed that the effect of EPA-E on hepatitis C complicated with hepatic steatosis is greater than that on hepatitis C not complicated with hepatic steatosis. Moreover, it is confirmed that the administration of interferon and EPA in combination has a greater effect on hepatitis C complicated with hepatic steatosis than the administration of interferon alone.

(2-3) Allowance of an Earlier Time at which Patients Become Negative for the Blood HCV-RNA Level.

Employing those hepatitis C patients as targets who were determined as non-responders or relapsers after interferon therapy, it is confirmed that the time at which the patients become negative for the blood HCV-RNA level is allowed to be earlier by the administration of EPA-E.

The patients to be tested are divided into two groups, EPA-E administered group and EPA-E non-administered group. To the EPA-E administered group, 1800 to 2700 mg/day of EPA-E is orally administered for at least two weeks after the patients were determined as non-responders or relapsers with respect to the interferon therapy. To the EPA-E non-administered group, none of EPA and derivatives thereof is administered during the testing period. Subsequently, the interferon therapy is conducted again on both groups. The dose, dosage interval, dosage period, and the like of interferon are specified as appropriate to the condition of a patient, side effects of the interferon, and so forth. The blood HCV-RNA level is measured in course of the administration of interferon. Data on the time after the start of interferon administration at which the patients became negative for the blood HCV-RNA level are collected to comparison between the two groups.

It is confirmed that the time at which the patients become negative for the blood HCV-RNA level shows a tendency to be earlier in the EPA-E administered group than the EPA-E non-administered group. For instance, the ratio of the patients becoming negative for the blood HCV-RNA level within 12 weeks after the start of interferon administration is increased.

Example 3

Improvement in Response Rate to Interferon Therapy in Patients Having Hepatitis C Complicated with Hypertriglyceridemia Out of the hepatitis C patients received interferon therapy (therapy with interferon and ribavirin applied in combination), those patients in whom the blood triglyceride level was less than 100 mg/dL before the start of treatment had a reduction in viral load (difference between the common logarithm value of the blood HCV-RNA level before interferon administration and the common logarithm value of the blood HCV-RNA level three days after the start of administration) of 2.042 on average three days after the start of the interferon therapy.

In contrast, those patients in whom the blood triglyceride level was not less than 150 mg/dL before the start of treatment had a reduction in viral load of 1.732 on average, which indicated that the effectiveness of the interferon therapy was low in the patients having hepatitis C complicated with hypertridlyceridemia.

On the patients having hepatitis C complicated with hypertriglyceridemia, the interferon therapy was then conducted along with the oral administration of 1800 to 2700 mg/day of EPA-E.

As a result, the reduction in viral load was 2.375 on average, that is to say, EPA-E improved the effectiveness of the interferon therapy in the patients having hepatitis C complicated with hypertriglyceridemia.

The reduction in viral load as obtained by a combined application of a statin drug together with EPA-E was 2.382 on average, a similar value to that obtained by a combined application of EPA-E alone.

The invention claimed is:

1. A method of treating a subject having interferon-resistant hepatitis C to effect a reduction in blood HCV-RNA level comprising administering to the subject a pharmaceutical composition comprising, as an active ingredient, at least one compound selected from the group consisting of ω-3 polyunsaturated fatty acids, pharmaceutically acceptable salts and esters thereof, thereby reducing the blood HCV-RNA level in combination with PEGylated-interferon, wherein the interferon-resistant hepatitis C is complicated with hypertriglyceridemia.

2. The method of claim 1, wherein the interferon-resistant hepatitis C is complicated with hepatic steatosis.

3. The method of claim 1, wherein the subject does not respond to interferon therapy.

4. The method of claim 1, wherein the subject has relapsed after interferon therapy was transiently effective.

5. The method of claim 1, comprising wherein the compound is selected from the group consisting of icosapentaenoic acid, docosahexaenoic acid, α-linolenic acid, pharmaceutically acceptable salts and esters thereof, and wherein the ratio of a (ethyl icosapentate+ethyl docosahexate) content to a total content of the fatty acids and derivatives thereof in the composition is not less than 84% by weight.

6. The method of claim 1, wherein the active ingredient is ethyl icosapentate, and wherein a ratio of the ethyl icosapentate content to a total content of the fatty acids and derivatives thereof in the composition is not less than 84% by weight.

7. The method of claim 1, wherein said at least one compound comprises not less than 70% by weight of the total fatty acids contained in said pharmaceutical composition.

8. The method of claim 1, wherein the subject does not respond to interferon therapy, wherein an interferon drug is administered in combination with ribavirin to said subject.

9. The method of claim 1, wherein the subject has relapsed after interferon therapy, wherein an interferon drug was administered in combination with ribavirin was transiently effective in said subject.

10. A method for improving response rate to PEGylated-interferon therapy in a subject having hepatitis C to effect a reduction in blood HCV-RNA level comprising administering a pharmaceutical composition comprising as an active ingredient at least one compound selected from the group consisting of ω-3 polyunsaturated fatty acids, pharmaceutically acceptable salts and esters thereof, thereby reducing the blood HCV-RNA level, wherein the interferon-resistant hepatitis C is complicated with hypertriglyceridemia.

11. The method of claim 10, wherein the hepatitis C is complicated with hepatic steatosis.

12. The method of claim 10, wherein the subject has not responded to interferon therapy alone.

13. The method of claim 10, wherein the subject has relapsed after interferon therapy was transiently effective.

14. The method of claim 10, wherein the compound is administered at least two weeks before the interferon therapy.

15. The method of claim 10, wherein said at least one compound comprises not less than 70% by weight of the total fatty acids contained in said pharmaceutical composition.

16. The method of claim 10, wherein the subject has not responded to interferon therapy, wherein an interferon drug is administered in combination with ribavirin to said subject.

17. The method of claim 10, wherein the subject has relapsed after interferon therapy, wherein an interferon drug was administered in combination with ribavirin was transiently effective in said subject.

* * * * *